US00PP23588P2

(12) United States Plant Patent
Giesen

(10) Patent No.: US PP23,588 P2
(45) Date of Patent: May 7, 2013

(54) *DIASCIA* PLANT NAMED 'DALA DEPSAM'

(50) Latin Name: *Diascia barbarae*
Varietal Denomination: Dala Depsam

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 439 days.

(21) Appl. No.: 12/924,305

(22) Filed: Sep. 24, 2010

(51) Int. Cl.
*A01H 5/00* (2006.01)

(52) U.S. Cl. ..... Plt./425

(58) Field of Classification Search ..... Plt./425
See application file for complete search history.

(56) References Cited

U.S. PATENT DOCUMENTS

PP20,905 P2 * 3/2010 Giesen ..... Plt./425

* cited by examiner

*Primary Examiner* — Susan McCormick Ewoldt
(74) *Attorney, Agent, or Firm* — Joshua L. Price

(57) ABSTRACT

A new *Diascia* plant named 'Data Depsam' particularly distinguished by the glossy medium red flowers with medium green foliage; excellent floriferousness and a dense upright habit; has superb heat tolerance and garden performance.

1 Drawing Sheet

Latin name of the genus and species of the plant claimed: *Diascia barbarae.*

Varietal denomination: 'Dala Depsam'.

BACKGROUND OF THE NEW PLANT

The present invention comprises a new *Diascia*, botanically known as *Diascia barberae*, and hereinafter referred to by the variety name 'Dala Depsam'.

'Data Depsam' is a product of a planned breeding program. The new cultivar has glossy medium red flowers with medium green foliage; excellent floriferousness and a dense upright habit; has superb heat tolerance and garden performance.

'Data Depsam' originated from a hybridization made in June 2005 in a controlled breeding environment in Andijk, Netherlands. The female parent was the unpatented, proprietary plant designated 'DS05-115-1' with fewer, larger orange flowers, lighter green foliage, and less branching.

The male parent of 'Data Depsam' was an unpatented, proprietary plant designated 'DS05-103-4' with less intense deep salmon colored flowers, shorter stems, and larger leaves. The resultant seeds were sown in October 2005.

'Data Depsam' was selected as one flowering plant within the progeny of the stated cross in the January, 2006 in a controlled environment in Andijk, The Netherlands.

The first act of asexual reproduction of 'Dala Depsam' was accomplished when vegetative cuttings were propagated from the initial selection in January 2006 in a controlled environment in Andijk, Netherlands.

BRIEF SUMMARY OF INVENTION

Horticultural examination of plants grown from cuttings of the plant initiated in Andijk, Netherlands, and continuing thereafter, has demonstrated that the combination of characteristics as herein disclosed for 'Data Depsam' are firmly fixed and are retained through successive generations of asexual reproduction.

'Data Depsam' has not been observed under all possible environmental conditions. The phenotype may vary significantly with variations in environment such as temperature, light intensity and day length.

Plant Breeder's Rights for this cultivar were applied for in Canada on Feb. 18, 2010 (10-6846) and in CVPO on Apr. 26, 2010 (2010/0898). 'Data Depsam' has not been made publicly available more than one year prior to the filing of this application.

The following traits have been repeatedly observed and are determined to be basic characteristics of the new variety. The combination of these characteristics distinguishes this Diascia as a new and distinct variety.

BRIEF DESCRIPTION OF THE PHOTOGRAPHS

The accompanying photographic drawing shows typical flower and foliage characteristics of 'Data Depsam' with colors being as true as possible with an illustration of this type. The photographic drawing shows 3 flowering potted plants of the new variety and a close-up of the flowers.

DETAILED BOTANICAL DESCRIPTION

The aforementioned photographs were taken in April 2010 of plants growing in a greenhouse trial in Gilroy, Calif. USA. These plants were growing in 8 inch basket pots and were approximately 15-16 weeks of age.

The plant descriptions and measurements were taken in mid July 2010 in Andijk, Netherlands. The plants were grown for 8 weeks in a greenhouse trial and then planted outdoors in window boxes with 5 plants in each box.

Color references are made to The Royal Horticultural Society Colour Chart (R.H.S.) 2001.

TABLE 1

DIFFERENCES BETWEEN THE NEW VARIETY 'DALA DEPSAM' AND A VARIETY OF MOST SIMILAR COLOR

| | 'Dala Depsam' | 'Diastina' (U.S. Plant Pat. No. 13,932) |
|---|---|---|
| Flower size: | Larger | Smaller |
| Foliage color: | Darker green | Lighter green |
| Stem thickness: | Thicker | Thinner |
| Flower color: | RHS 39A | RHS 25C |
| Spur length: | Shorter | Little longer |

TABLE 2

DIFFERENCES BETWEEN THE NEW VARIETY 'DALA DEPSAM' AND A SIMILAR OR SAME PEDIGREE

| | | 'Dala Orange' (U.S. Plant Pat. No. 20,905) |
|---|---|---|
| Flower color: | RHS red group | RHS orange-red group |
| Flower diameter: | Narrower | Wider |
| Spur length: | Slightly shorter | Slightly longer |
| Spur color: | More orange-red with red-purple apex | Red-pink |
| Bud color: | More pinkish | Orange-red |

Plant:

*Form, growth and habit*.—Initially compact, rounded and mounded; then becoming a little some-what trailing; freely branching, terminal pinching enhances branching habit.

*Plant height*.—15 cm.

*Plant height* (*inflorescence included*).—23 cm.

*Plant width*.—48 cm.

Roots:

*Number of days to initiate and develop roots*.—16-20 days at about 22 degrees C.

*Type*.—Fine, fibrous, free branching.

*Color*.—RHS N155B but whiter.

Foliage:

*Arrangement*.—Simple; decussate.

*Immature, leaf color, upper surface*.—RHS 141B.

*Lower surface*.—RHS 138B.

*Mature, leaf color, upper surface*.—RHS 135A.

*Lower surface*.—RHS 146A.

*Length*.—2-2.5 cm.

*Width*.—1.9-2.2 cm.

*Shape*.—Deltoid.

*Base shape*.—Truncate.

*Apex shape*.—Acute.

*Margin*.—Weakly dentate.

*Texture, upper surface*.—Shiny and glabrous.

*Lower surface*.—Glabrous.

*Color of veins, upper surface*.—RHS 135A.

*Color of veins, lower surface*.—RHS 135A.

*Petiole color*.—RHS 141C.

*Length*.—0.5 cm.

*Diameter*.—0.2 cm.

*Texture*.—Glabrous.

Stem:

*Quantity of main branches*.—35-45.

*Color of stem*.—RHS 141B.

*Length of stem*.—20-25 cm.

*Diameter*.—0.25-0.3 cm.

*Length of internodes*.—2.5-3.0 cm.

*Texture*.—Glabrous.

*Color of raceme*.—RHS 141B.

*Length of raceme*.—5-7 cm.

*Diameter of raceme*.—0.2 cm.

*Texture*.—Glabrous.

*Pedicel color*.—RHS 59A.

*Pedicel length*.—0.7-1.1 cm.

*Pedicel diameter*.—0.05 cm.

*Pedicel texture*.—Finely pubescent.

Inflorescence:

*Type*.—Terminal raceme with flowers in an alternate arrangement.

*Blooming habit*.—Flowering freely and continuously from the spring into the fall.

*Quantity of inflorescences per plant*.—70-80 in various stages.

*Quantity of inflorescences per lateral stem*.—14-18 flowers and buds in various stages of development.

*Lastingness of individual blooms on the plant*.—4-5 days depending on the weather and temperatures.

*Fragrance*.—None.

Bud (when first opening/showing color):

*Color*.—RHS 65D and RHS 61A.

*Length*.—0.3 cm.

*Width*.—0.5 cm.

*Shape*.—Conical.

Immature flower:

*Diameter*.—1.4 cm.

*Color, upper surface*.—RHS 39A.

*Lower surface*.—RHS 39C.

Mature flower:

*Hortizontal diameter*.—1.8-2.0 cm.

*Vertical height*.—2-2.2 cm.

*Depth*.—0.4 cm.

*Color, upperside*.—RHS 39A.

*Underside*.—RHS 39C.

*Corolla tube color inside*.—RHS 7A.

*Outside*.—RHS 9D.

*Corolla tube length*.—0.2 cm.

*Corolla texture, outside*.—Rugose.

*All lobes, apex*.—Rounded.

*Base*.—Fused.

*Margin*.—Entire.

*Texture*.—Glabrous.

*Upper lobes, size, length*.—0.4 cm.

*Width:* 0.5 cm.

*Lateral lobes, length:* 0.3 cm.

*Width*.—0.5 cm.

*Lower lobes, length*.—1-1.2 cm.

*Width*.—1.3-1.5 cm.

*Spur, color*.—RHS 39C; RHS 59A at the apex.

*Length*.—0.6 cm.

*Width*.—0.2 cm at the widest point.

*Curvature*.—Directed downwards.

Calyx: Star-shaped with (5) sepal lobes slanting downward.

*Sepal color*.—RHS 139A.

*Sepal length*.—0.1 cm.

*Sepal width*.—0.1 cm.

*Sepal shape*.—Lanceolate.

*Sepal apex*.—Acute.

*Sepal texture*.—Weakly hirsuate.

*Sepal anthocyanin*.—Slightly at sepal apex of about RHS 59A.

Reproductive organs:

*Stamens*.—4: arching towards and somewhat twisting around the pistil.

*Filament color*.—RHS 59A.

*Filament length*.—0.25 cm.

*Filament diameter*.—0.1 cm.

*Anther color*.—RHS 7A.

*Anther length*.—0.05 cm.

*Pollen color*.—RHS 7A.

*Pollen amount*.—Abundant.

*Pistil*.—1 per flower.

*Pistil length*.—0.3 cm.

*Style color*.—RHS 145C.

*Style length*.—0.3 cm.

*Stigma color*.—RHS 13B.

*Fertility/seed set*.—Has not been observed on this hybrid.

Disease/pest resistance: Disease/pest resistance has not been observed on this hybrid.

What is claimed is:

1. A new and distinct variety of *Diascia* plant named 'Dala Depsam' substantially as illustrated and described herein.

* * * * *

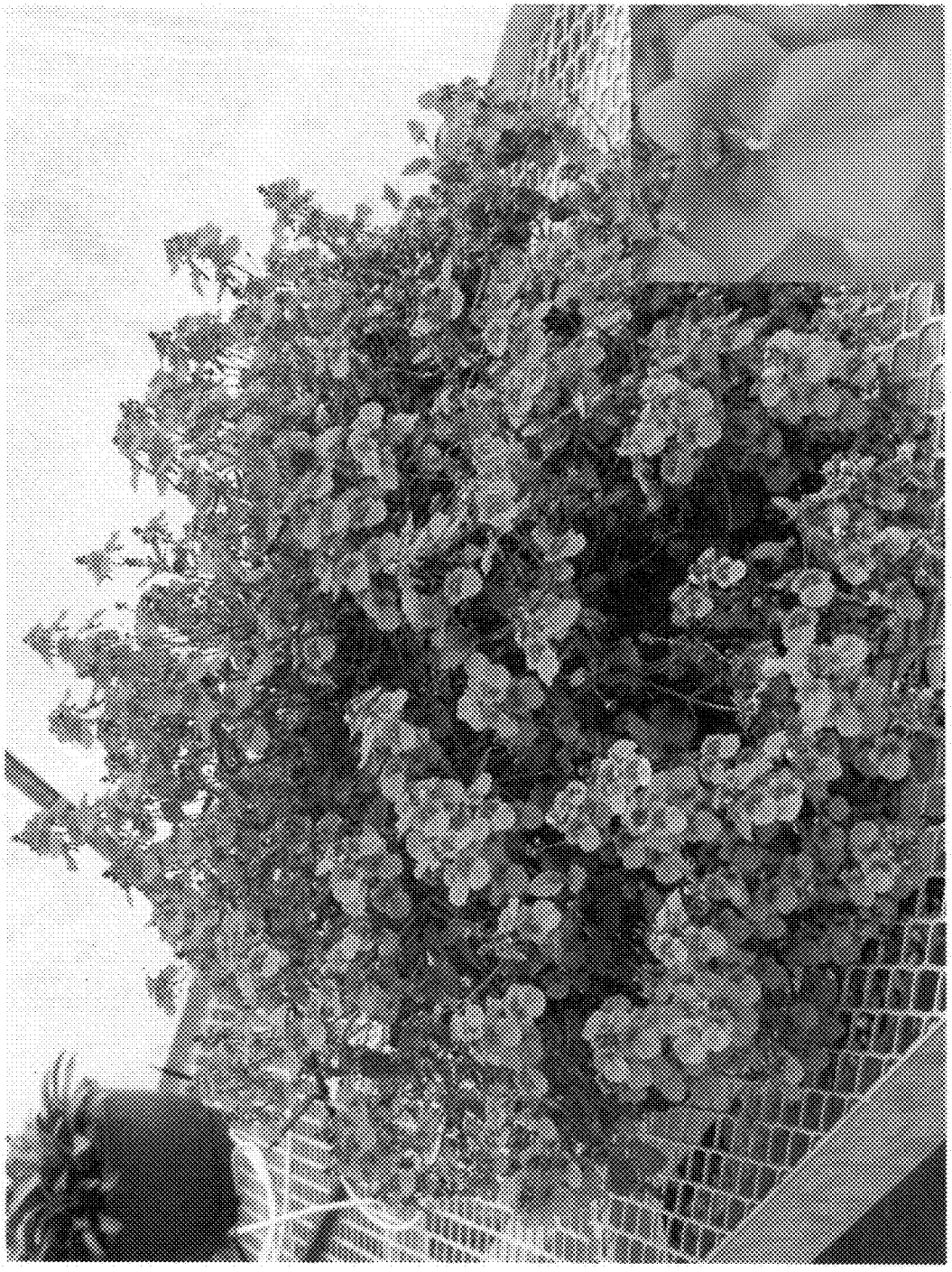

UNITED STATES PATENT AND TRADEMARK OFFICE

CERTIFICATE OF CORRECTION

PATENT NO. : PP23,588 P2
APPLICATION NO. : 12/924305
DATED : May 7, 2013
INVENTOR(S) : Giesen It is certified that error appears in the above-identified patent and that said Letters Patent is hereby corrected as shown below:

Title Page, Item (57), in the ABSTRACT, delete "'Data Depsam'" and insert therefor --'Dala Depsam'--

In the Specification

At column 1, line 10, delete "'Data Depsam'" and insert therefor --'Dala Depsam'--

At column 1, line 15, delete "'Data Depsam'" and insert therefor --'Dala Depsam'--

At column 1, line 20, delete "'Data Depsam'" and insert therefor --'Dala Depsam'--

At column 1, line 24, delete "'Data Depsam'" and insert therefor --'Dala Depsam'--

At column 1, line 37, delete "'Data Depsam'" and insert therefor --'Dala Depsam'--

At column 2, line 1, delete "'Data Depsam'" and insert therefor --'Dala Depsam'--

At column 2, line 8, delete "'Data Depsam'" and insert therefor --'Dala Depsam'--

At column 2, line 21, delete "'Data Depsam'" and insert therefor --'Dala Depsam'--

Signed and Sealed this
Twenty-fifth Day of June, 2013

Teresa Stanek Rea

Teresa Stanek Rea
*Acting Director of the United States Patent and Trademark Office*